US009611104B2

United States Patent
Murakami

(10) Patent No.: US 9,611,104 B2
(45) Date of Patent: Apr. 4, 2017

(54) SORTING APPARATUS AND VESSEL SORTING METHOD

(71) Applicant: HIRATA CORPORATION, Shinagawa-ku (JP)

(72) Inventor: Seigo Murakami, Shinagawa-ku (JP)

(73) Assignees: HIRATA CORPORATION, Tokyo (JP); SYSMEX CORPORATION, Hyogo (JP)

( * ) Notice: Subject to any disclaimer, the term of this patent is extended or adjusted under 35 U.S.C. 154(b) by 988 days.

(21) Appl. No.: 13/707,318

(22) Filed: Dec. 6, 2012

(65) Prior Publication Data

US 2013/0142596 A1    Jun. 6, 2013

(30) Foreign Application Priority Data

Dec. 6, 2011    (JP) ................. 2011-267398

(51) Int. Cl.
*G01N 35/04*    (2006.01)
*B65G 49/00*    (2006.01)
*G01N 35/02*    (2006.01)

(52) U.S. Cl.
CPC ............ *B65G 49/00* (2013.01); *G01N 35/04* (2013.01); *G01N 35/026* (2013.01); *G01N 2035/0415* (2013.01); *G01N 2035/0465* (2013.01); *Y10T 436/114165* (2015.01)

(58) Field of Classification Search
None
See application file for complete search history.

(56) References Cited

FOREIGN PATENT DOCUMENTS

| JP | 4-009668 A | 1/1992 |
|----|------------|--------|
| JP | 04-104058 A | 4/1992 |
| JP | 05-142232 A1 | 6/1993 |
| JP | 09-015245 A | 1/1997 |
| JP | 3 047571 B2 | 5/2000 |

OTHER PUBLICATIONS

Translation of JP 04-009668A to inventor Kanji Murakami and applicant Teijin Seiki Co., Ltd., originally published on Jan. 14, 1992.*
Software translation of JP 09-15245 (A) to S. Arimadono; Jan. 17, 1997.*

* cited by examiner

*Primary Examiner* — Yelena G Gakh
*Assistant Examiner* — Michelle Adams
(74) *Attorney, Agent, or Firm* — Buchanan Ingersoll & Rooney PC

(57) ABSTRACT

A sorting apparatus includes: a sorting device receiving and transporting a rack carrying vessels and transferring vessels from the rack to predetermined vessel loading portions; and a delivery device delivering the rack to the sorting device. The sorting device includes: a rack receiving unit capable of moving reciprocally between a rack delivery position where the rack is delivered and a sorting position where the vessels are loaded into the predetermined vessel loading portions; a transfer machine transferring the vessels from the rack on the rack receiving unit to the predetermined vessel loading portions; and a transportation mechanism on which the rack delivering unit and the transfer machine are installed. The transportation mechanism is installed so as to be capable of moving in a transportation direction in which rack receiving unit moves reciprocally. The transfer machine is capable of moving in a direction perpendicular to the transportation direction.

7 Claims, 11 Drawing Sheets

SORTING APPARATUS AND VESSEL SORTING METHOD

FIELD OF THE INVENTION

The present invention relates to a sorting apparatus that sorts and conveys vessels, such as test tubes or blood collection tubes, which hold specimens to transfer destinations in accordance with conditions such as the specimen type and/or test type.

DESCRIPTION OF THE RELATED ART

Among known sorting apparatuses for classifying vessels holding specimens, there is a sorting apparatus including a loading bench as a sorting destination for the specimens and a header that moves above the loading bench, such header including a gripping unit for holding a bottomless cassette and a dropper unit for pressing out specimen vessels loaded onto the held cassette to below the held cassette (see Patent Document 1)

Known sorting apparatuses also include a clinical test apparatus including a specimen introducing unit in which is set a rack for supporting vessels to which specimen identification numbers have been attached, a rack ID detection unit, a specimen ID detection unit, an empty rack supplying unit, a specimen-distributed rack storage unit, and an empty rack storage unit. Such clinical test apparatus also includes a specimen vessel assigning means equipped with an X direction movement arm, a Y direction movement arm, and a grip device for gripping specimen vessels, and automatically sorts individual specimen vessels out of the plurality of specimen vessels into corresponding types (see Patent Document 2).

Patent Document 1
  Japanese Laid-Open Patent Publication No. H04-9668
Patent Document 2
  Japanese Patent No. 3,047,571

SUMMARY OF THE INVENTION

However, the former sorting apparatus described above is configured so as to convey vessels that are housed in a bottomless rack to predetermined sorting destinations by pressing the vessels downward out of the rack using the dropper unit. Accordingly, normal racks that are fitted with bottoms cannot be used and it is necessary to specially provide bottomless racks, giving this apparatus poor compatibility with existing equipment. In addition, since the apparatus is constructed so as to press vessels such as test tubes downward toward the bottom side of a rack, if covers with a larger diameter than the vessels are attached, there is the risk of such covers catching when the vessels are downwardly pressed out. In addition, if a vessel being downwardly pressed out catches on the rack or the sorting bench and/or cannot be pressed out in the downward direction, it is not easy to upwardly remove such vessel, which means it is time-consuming to restore the sorting apparatus to working order.

With the latter clinical test apparatus, the introduced specimen vessels are gripped by the grip device, the grip device is moved in the X direction and the Y direction, and after gripped specimen vessels have been conveyed to the sorting destination, the specimen vessels are stored in a specimen-distributed rack storage unit. With such an apparatus, if, to improve the take time of sorting, the grip device gripping the specimen vessels is moved at high speed to increase the conveying speed, a larger load will be placed on the grip device when the grip device starts and stops an operation. If the apparatus is made more rigid to withstand such load, the apparatus size will increase, as will the apparatus weight.

The present invention was conceived in view of the above problem and aims to provide a sorting apparatus and a sorting method that have superior applicability through the ability to use normal racks with fitted bottoms and also reduce the load applied to a vessel transporting means to a minimum.

A sorting apparatus according to the present invention includes: a sorting device receiving and transporting a rack on which a plurality of vessels are loaded and transferring the vessels loaded on the rack to predetermined vessel loading portions; and a delivery device delivering the rack to the sorting device, wherein the sorting device includes: a rack receiving unit installed so as to be capable of moving reciprocally between a rack delivery position where the rack is delivered from the delivery device and a sorting position where the vessels are loaded into the predetermined vessel loading portions; a transfer machine transferring the vessels loaded on the rack on the rack receiving unit to the predetermined vessel loading portions; and a transportation mechanism on which the rack delivering unit and the transfer machine are installed, the transportation mechanism is installed so as to be capable of moving in a transportation direction that is a direction of reciprocal movement of the rack receiving unit, and the transfer machine is capable of moving in a perpendicular direction that is perpendicular to the transportation direction.

The rack may include a plurality of vessel insertion portions that enable the vessels to be inserted and removed from above the rack, the vessel loading portions that are sorting destinations of the vessels may enable the vessels to be inserted and removed from above, the transfer machine may include a vessel gripping arm installed so as to be capable of advancing and retreating in an up-down direction, and the vessel gripping arm may grip a vessel loaded in one of the vessel insertion portions of the rack of the rack receiving unit, upwardly remove the vessel from an access opening, and transfer the vessel to a vessel loading portion that is the sorting destination by inserting the vessel into an insertion hole of the vessel loading portion from above.

The vessel gripping arm may be capable of advancing to and retreating from a removal lowered position where a vessel loaded in a vessel insertion portion of the rack on the rack delivery unit is removed and an insertion lowered position where the removed vessel is inserted into the vessel loading portion that is the sorting destination and is disposed further below the rack delivery unit, a rack receiving mechanism installed on the transportation mechanism may include the rack receiving unit and a guide member that allows the rack receiving unit to move in only the transportation direction, and the rack receiving unit may be capable of moving to a vessel removal position where a vessel loaded into a vessel insertion portion of the rack received by the rack receiving unit is capable of being removed by the vessel gripping arm and to a withdrawn position where interference between the vessel gripping arm that is lowered to the insertion lowered position and'the rack receiving unit is prevented.

The rack receiving unit may also be attached to the transportation mechanism so as to be capable of moving to a rack receiving position when the rack is delivered from the delivery device.

The rack receiving mechanism may further include a hold member that holds the rack that has been loaded on the rack receiving unit that has moved to a vessel removing position by clamping in concert with the rack receiving unit.

The hold member may be provided so as to be capable of moving between a separated position that is separated from the rack in a state where the rack is loaded on the rack receiving unit positioned at the rack receiving position and a contact position where the hold member contacts the rack loaded on the rack receiving portion positioned at the vessel removal position and holds the rack by operating in concert with the rack receiving unit, and the rack receiving mechanism may further include an energizing device energizing the hold member toward the separated position.

A movement range of the transportation mechanism installed so as to be movable in the transportation direction may be inside a reciprocal movement range of the rack receiving unit that is capable of moving to the rack delivery position and the sorting position, and may be shorter than the reciprocal movement range.

The delivery device may be a lifter provided so as to be capable of moving up and down between a lifter lowered position where the rack to be delivered is loaded on the delivery device and a lifter raised position for delivering the rack to the rack receiving unit at the rack delivery position.

The present invention also provides a vessel sorting method for a sorting apparatus including a transportation mechanism capable of reciprocal movement in a predetermined direction, a rack receiving unit provided on the transportation mechanism, and a transfer machine supported on the transportation mechanism so as to be capable of moving in a perpendicular direction that is perpendicular to a direction of reciprocal movement of the transportation mechanism, the vessel sorting method including: a first transportation process where, after a rack on which a plurality of vessels are loaded has been received by the rack receiving unit, the transportation mechanism on which the rack receiving unit is installed transports the rack by linearly moving in a same direction as the direction of reciprocal movement from a rack receiving position to a transfer position where a vessel loaded on the rack is removed; a vessel removal preparation process of moving the rack receiving unit in the direction of reciprocal movement and positioning the rack receiving unit at a lowered position on a movement path of the transfer machine which is installed so as to be capable of movement in the perpendicular direction so as to position a vessel loaded on the rack loaded on the rack removing unit at the lowered position; a vessel removing process removing a predetermined vessel out of the vessels moved to the lowered position by raising and lowering a vessel gripping arm provided in the transfer machine; a vessel transfer preparation process positioning a predetermined vessel gripped by the vessel gripping arm above a vessel loading unit by moving the transfer machine that has removed the vessel in the perpendicular direction; and a vessel transfer process lowering the vessel gripping arm to load the predetermined vessel gripped by the vessel gripping arm into the vessel loading portion.

The vessel transfer preparation process may include: a second transportation process that moves the transfer machine above the vessel loading portion positioned below the rack receiving unit positioned at a lowered position on a movement path of the transfer machine; and a withdrawing process that moves the rack receiving unit at the lowered position on the movement path of the transfer machine toward the rack receiving position to withdrawn the rack receiving unit from the lowered position.

Since the sorting apparatus and sorting method according to the present invention do not place limitations on the form and the like of a rack capable of being received by a rack receiving unit and allow the use of existing racks with fitted bottoms already in widespread use, such apparatus and method have superior applicability.

In the sorting apparatus, since the rack is transported in the direction of reciprocal movement by the rack receiving unit capable of moving reciprocally between the rack receiving position and a sorting position for a rack and the rack is transported in a perpendicular direction that is perpendicular to the transportation direction by the transfer machine capable of moving in the perpendicular direction, the load applied to the rack receiving unit and the transfer machine is reduced to a minimum when starting and stopping movement. A sorting apparatus with such configuration is suited to transportation at higher speed.

With the sorting method, since the vessel is transported by moving the rack receiving unit that has received a rack in the direction of reciprocal movement and the transfer machine is moved in the perpendicular direction after a vessel is removed from the rack using a vessel gripping arm of the transfer machine to position the gripped vessel above a vessel loading portion, the load applied to the rack receiving unit and the transfer machine is reduced to a minimum when starting and stopping movement. A sorting apparatus with such configuration is suited to transportation at higher speed.

DESCRIPTION OF THE PREFERRED EMBODIMENTS

Preferred embodiments of a sorting apparatus according to the present invention will now be described with reference to the attached drawings.

Figure 1:
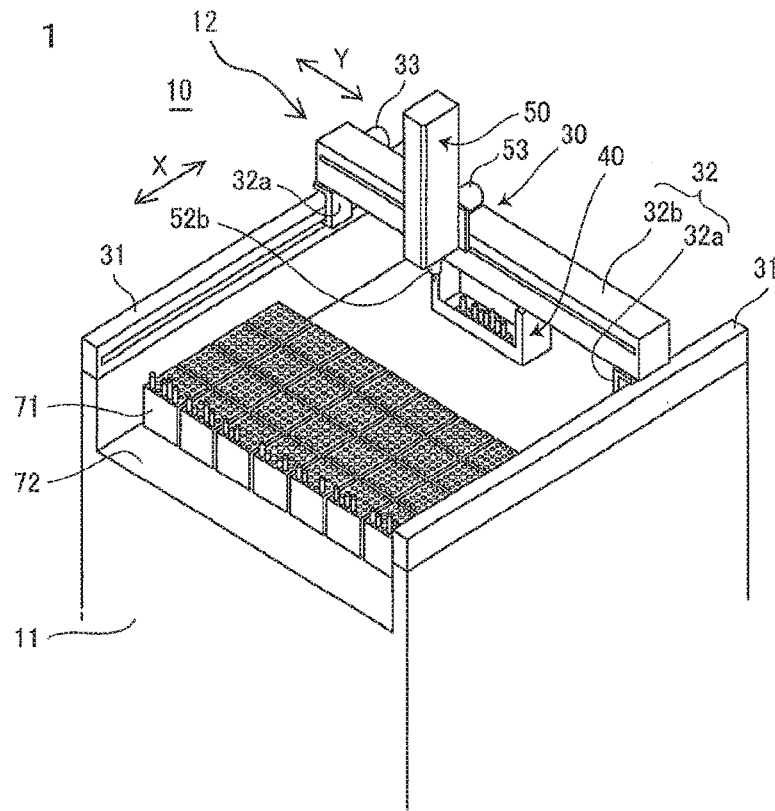
FIG. 1 is a perspective view showing a sorting apparatus according to an embodiment of the present invention.
Figure 20:
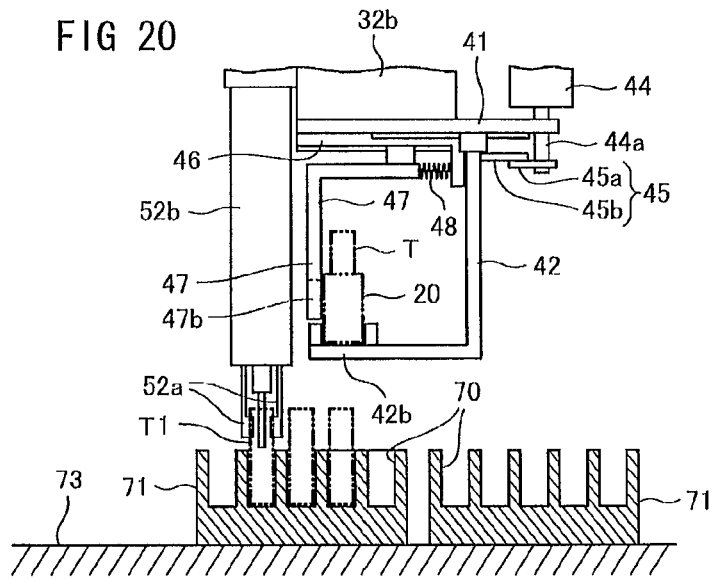
FIG. 20 is a side view diagram showing a main configuration of the sorting apparatus and is useful in explaining the operation of the sorting apparatus.
Figure 21:
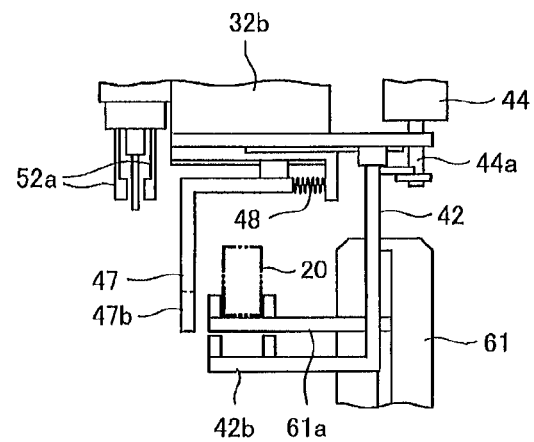
FIG. 21 is a side view diagram showing a main configuration of the sorting apparatus and is useful in explaining the operation of the sorting apparatus.
Figure 22:
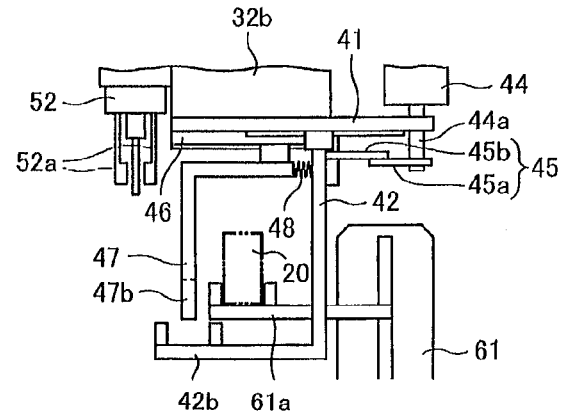
FIG. 22 is a side view diagram showing a main configuration of the sorting apparatus and is useful in explaining the operation of the sorting apparatus.
Figure 26:
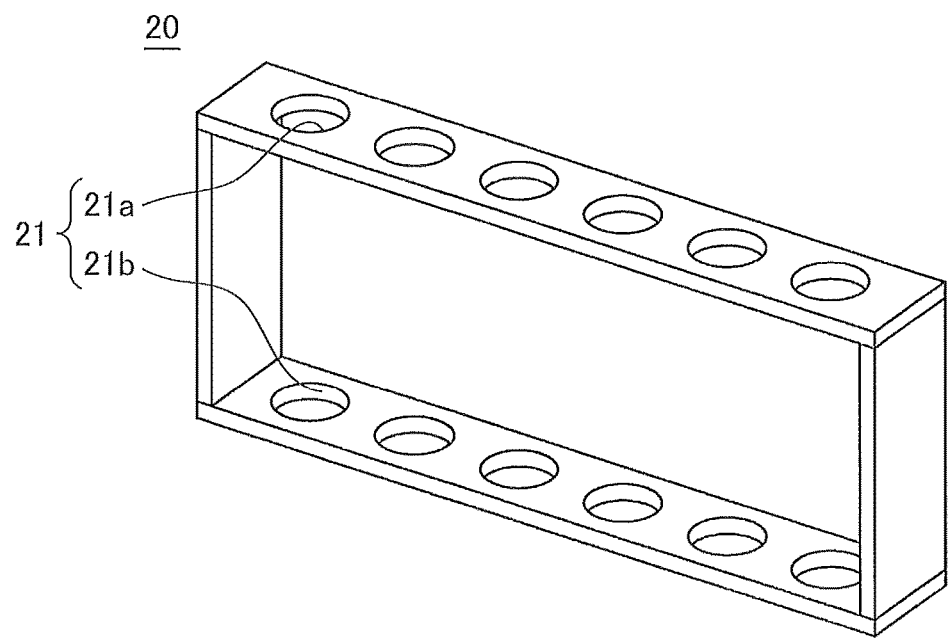
FIG. 26 is a perspective view showing a rack to be used in the sorting apparatus.

The sorting apparatus 10 shown in FIG. 1 is an apparatus that conveys a rack 20 (see FIG. 3 and FIG. 26) on which a plurality of blood collection tubes T (see FIG. 3) have been loaded and sorts the blood collection tubes T by removing the blood collection tubes T from the rack 20 and transferring such tubes to predetermined blood collection tube loading portions 70 (see FIG. 20).

Figure 2:
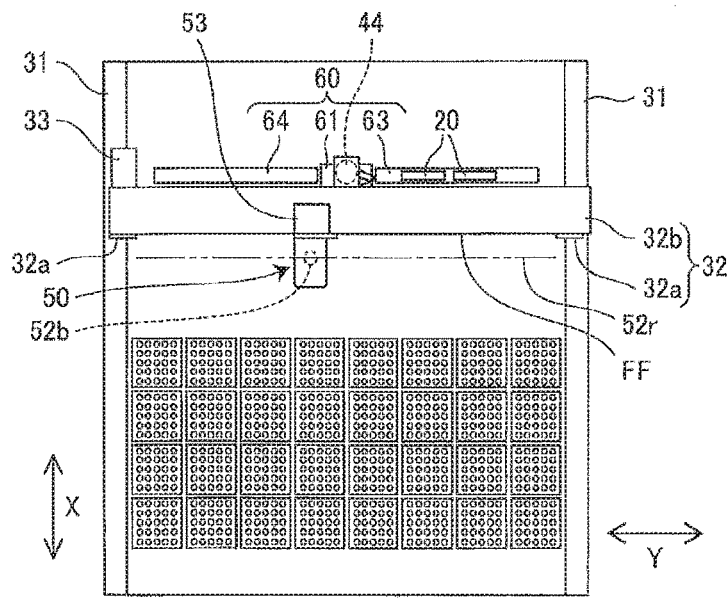
FIG. 2 is a plan view showing the sorting apparatus in FIG. 1.
Figure 24:
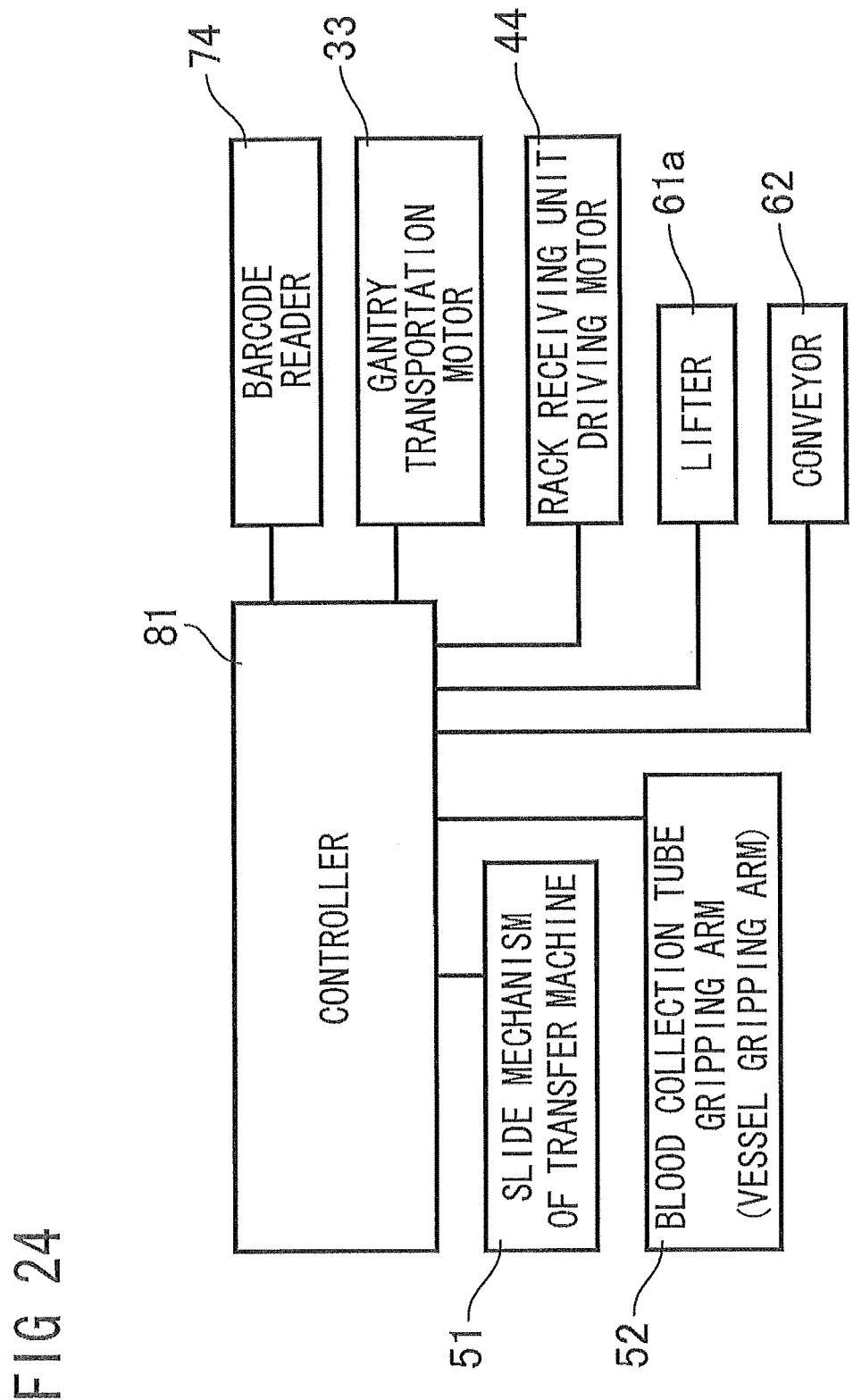
FIG. 24 is a block diagram showing a control unit of the sorting apparatus in FIG, 1.
Figure 25:
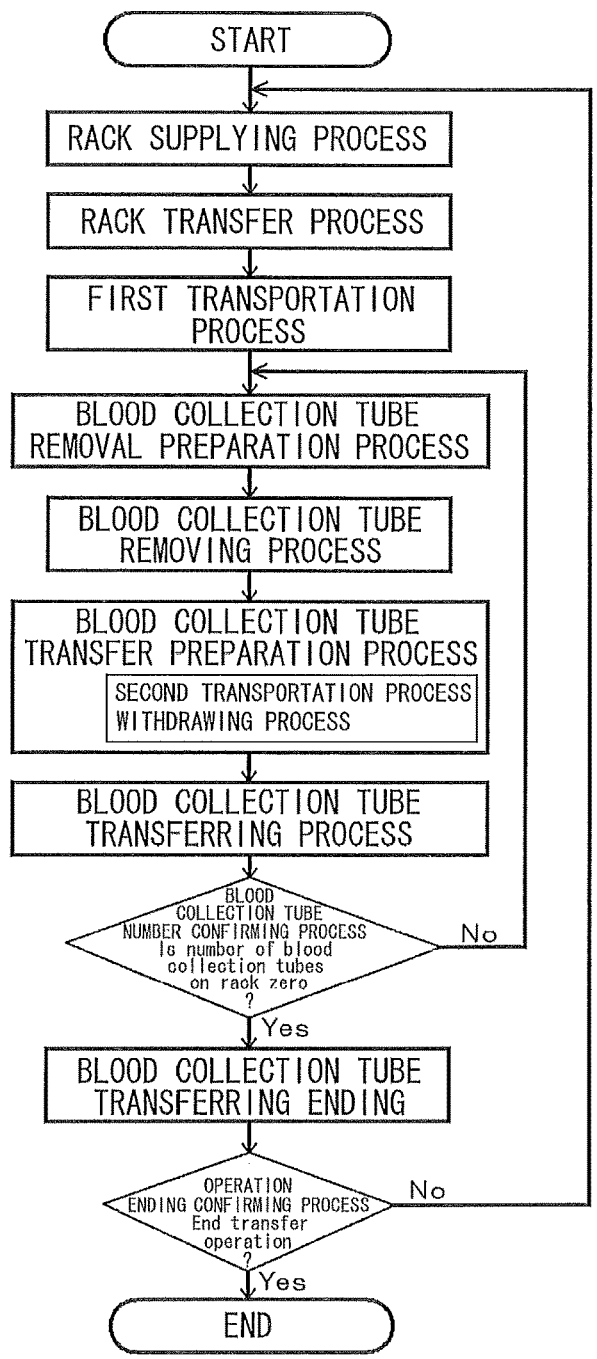
FIG. 25 is a flowchart useful in explaining the operation of the sorting apparatus.

The sorting apparatus 10 includes an apparatus base portion 11, a sorting device 12 installed on the base portion 11, a rack delivery device 60 (see FIG. 2) that delivers a rack 20, on which a plurality of blood collection tubes T have been loaded, to the sorting device 12, a sorting bench 72 on which sorting cassettes 71 equipped with a plurality of blood collection tube loading portions (or "vessel loading portions") 70 are installed, a barcode reader (or "information reading device") 74 (see FIG. 24) reading identification information (or "sorting conditions") such as barcodes displayed on the outer circumferences of the blood collection tubes T, and a controller 81 that controls the operations of the sorting device 12 and the rack delivery device 60 based on the read information or the like.

The sorting bench 72 on which the sorting cassettes 71 are installed is disposed on the upper surface at the front (the lower left side in FIG, 1) that is one end of the base portion 11, and the rack delivery device 60 is installed at the rear (the upper right side of FIG. 1) that is the other end of the base portion 11. Note that the sorting apparatus 10 according to the present embodiment may further include a rack storage unit (not shown) in which racks 20 in which the blood collection tubes T to be sorted are loaded and/or empty racks 20 are loaded. In such case, the racks 20 are supplied from such rack storage unit to the rack delivery device 60.

Note that the rack 20 (see FIG. 26) used in the present embodiment is a well-known rack that includes a plurality of blood collection tube insertion portions 21 (see FIG. 6 and FIG. 23), each with an access opening 21a that is open to above and a bottom holding portion 21b that holds a bottom portion of a blood collection tube T that has been inserted from the access opening 21a. In this way, the sorting apparatus 10 according to the present embodiment is capable of handling racks 20 that are already in widespread use without needing special racks, giving this apparatus superior compatibility with existing equipment.

When such a rack 20 is used, a blood collection tube T is loaded onto the rack 20 by gripping the upper portion of the blood collection tube T with a blood collection tube gripping arm 52b, described later, or the like, inserting the bottom portion of the blood collection tube T from above into the access opening 21a of a blood collection tube insertion portion 21, and then having the bottom portion contact and sit upon the bottom holding portion 21b of the blood collection tube insertion portion 21. The blood collection tube T inserted into the rack 20 is subsequently removed from the rack 20 by gripping and lifting the upper portion of the blood collection tube T using the blood collection tube gripping arm 52b or the like.

Regarding the blood collection tube loading portions 70 of the sorting cassettes 71, in the same way as the rack 20, a sorting cassette 71 includes a plurality of blood collection tube loading portions 70 (see FIG. 20), each with an access opening that is open to above and a bottom supporting portion that supports the bottom portion of a blood collection tube T that has been inserted from the access opening. This means that by carrying out the same operation as described above, it is possible to insert and remove a blood collection tube T into and from a sorting cassette 71.

Since the barcode reader 74 is a well-known apparatus that acts as an information reading device, detailed description thereof is omitted here. The format of the identification information is not limited to a format displayed as a barcode (a one-dimensional code) and it is possible to use a known information displaying format or information storing format, such as a matrix-like two-dimensional code called a "QR code" (registered trademark) or a format where information is stored in a small-scale radio wave transmitter, such as an IC tag. With barcodes or two-dimensional codes, information displaying media such as stickers displaying such codes may be stuck onto the outer circumferences of the blood collection tubes T. In the case of a small-scale radio wave transmitter, a radio wave transmitter storing identification information may be attached, so as to hang for example, to a blood collection lube T.

As shown in FIG. 1, the sorting device 12 includes a transportation unit 30 installed on the base portion 11, a rack receiving unit 40 installed on the transportation unit 30, and a transfer machine 50 installed on the transportation unit 30.

The transportation unit 30 includes a pair of transportation rails 31,31 installed at both left and right ends of the base portion 11, a gantry shaft (transportation mechanism) 32 installed so as to be capable of moving back and forth in the X direction (hereinafter also referred to as the "transportation direction") along the transportation rails 31,31, and a transportation motor 33 that is a driving device for the gantry shaft 32.

The gantry shaft (transportation mechanism) 32 includes sliders 32a that move along the left and right transportation rails 31,31 and a beam portion 32b that is supported at both ends on the sliders 32a,32a. Note that the beam portion 32b is a member that extends in a perpendicular direction Y that is perpendicular to the transportation direction X.

Figure 23:
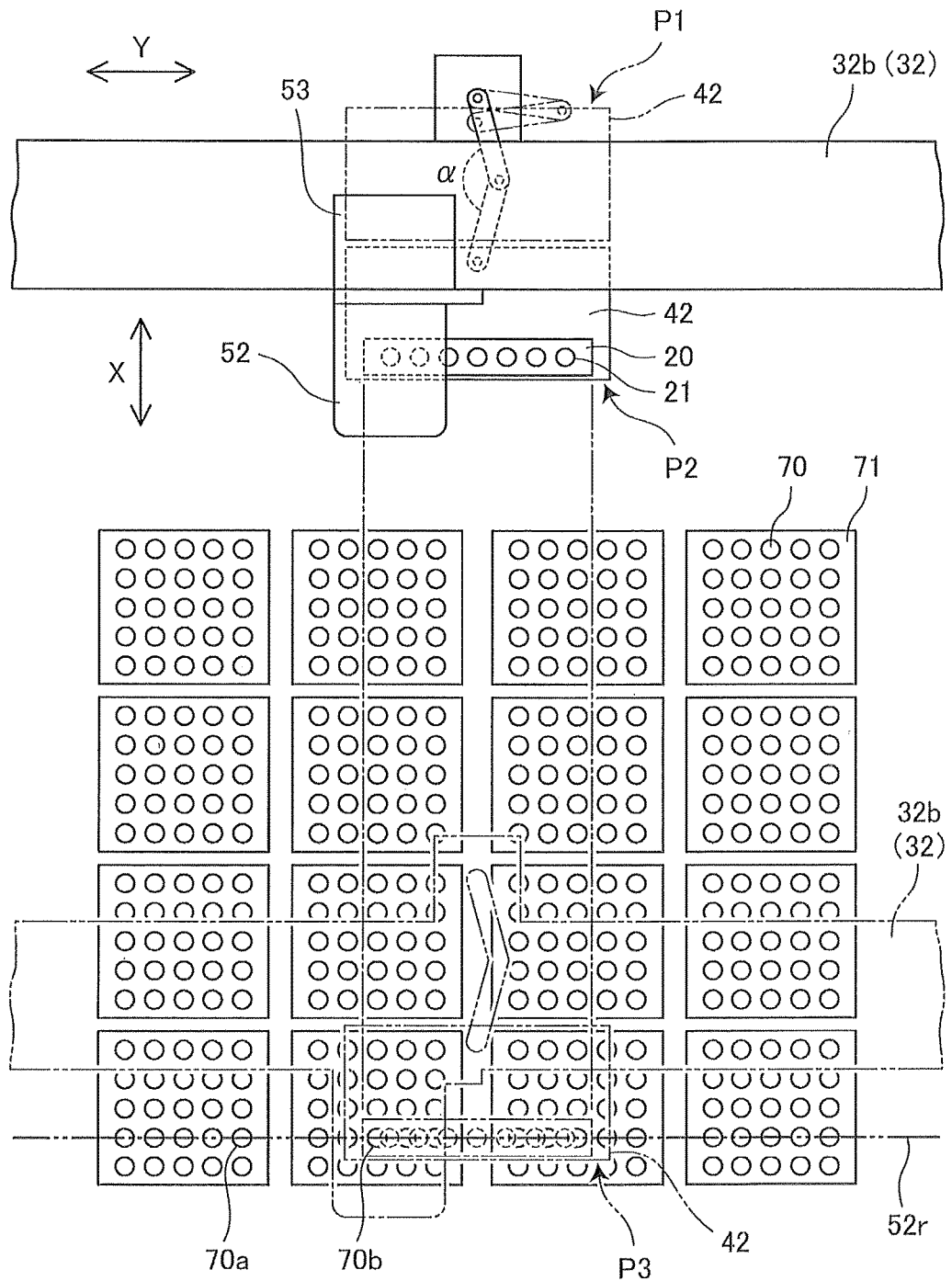
FIG. 23 is a schematic plan view useful in explaining positions of a gantry shaft and the rack receiving member.

The gantry shaft 32 is capable of reciprocally moving in the transportation direction X along the transportation rails 31,31 between a retreated position (refer to the position of the gantry shaft 32 shown by the solid line in FIG. 23) that is near the rack delivery device 60 (see FIG. 2) and an advanced position (refer to the position of the gantry shaft 32 shown by the dot-dot-dash line in FIG. 23) that is a position above the sorting bench 72.

Note that the expression "retreated position" refers to the position of the gantry shaft 32 when a rack receiving member 42 receives a rack 20 from a lifter 61a, described later (i.e., the position of the transportation mechanism when a rack is received).

The expression "advanced position" refers to the position of the gantry shaft 32 when a blood collection tube T is transferred to a predetermined blood collection tube loading portion 70 by the transfer machine 50, described later (i.e., the position of the transportation mechanism when a blood collection tube is transferred).

In this way, the movement range of the gantry shaft 32 in the transportation direction X is a range between a rack delivery position of the rack receiving member 42 described later (refer to the position of the rack receiving member 42 shown by P1 in FIG. 23) and a sorting position (refer to the position of the rack receiving member 42 shown by P3 in FIG. 23). That is, the range of movement in the transportation direction X of the gantry shaft 32 is a shorter range than the range of reciprocal movement of the rack receiving member 42, described later. In this way, since the gantry shaft 32 that is the most basic and heaviest member out of the members that construct the sorting device 12 has the shortest movement range, it is possible to reduce the length of the rails 31,31 and to suppress the vibration due to bending of the rails to a minimum.

Figure 3:
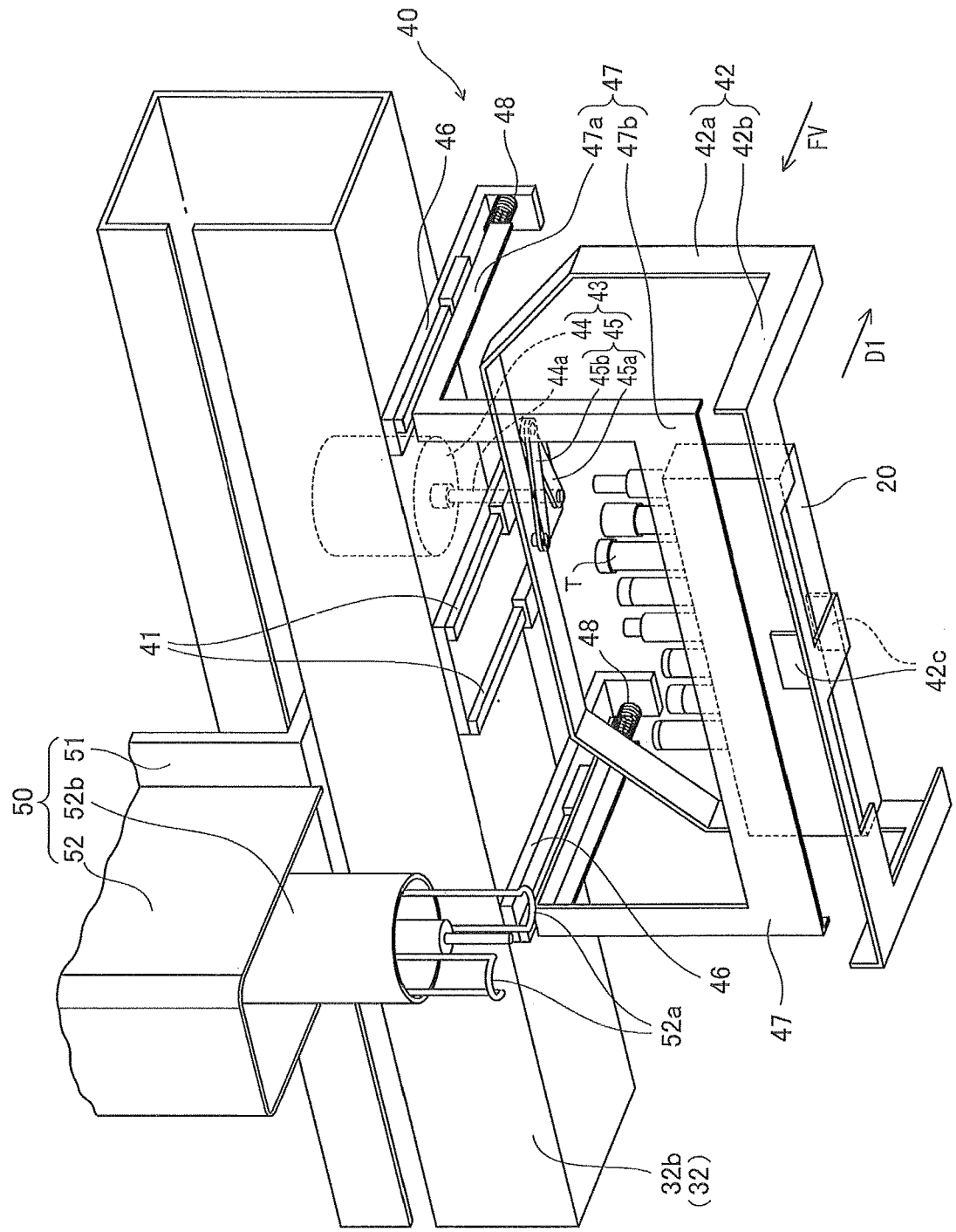
FIG. 3 is a perspective view showing a rack receiving member provided in the sorting apparatus in FIG. 1.

The rack receiving unit 40 includes a left and right pair of first guide rails 41,41 that are installed on the gantry shaft 32 and, as shown in FIG. 3, are installed so as to extend in the transportation direction X, the rack receiving member (or "rack receiving unit") 42 that is installed so as to be capable of moving reciprocally along the first guide rails 41,41, a rack receiving unit driving unit (or "guide member") 43 for moving the rack receiving member 42 only in the transportation direction, a left and right pair of second guide rails 46,46 installed so as to extend in the transportation direction X, a rack hold member (hereinafter, hold member) 47 installed so as to be capable of moving along the second guide rails 46,46, and coil springs (or "energizing members", hereinafter "springs") 48 that apply an energizing force to the hold member 47 in a direction D1 toward the rear in the transportation direction (see FIG. 3).

The first guide rails 41,41 and the second guide rails 46,46 are installed on a lower surface of the beam portion 32b of the gantry shaft 32, and the rack receiving member 42 and the hold member 47 are both attached so as to be suspended below the corresponding guide rails.

The rack receiving unit driving unit 43 includes a rack receiving unit driving motor 44 that is installed on a rear surface of the beam portion 32b and a retractable arm 45 that is connected to an output shaft 44a of the motor 44 and the rack receiving member 42. The retractable arm 45 has a link mechanism where two arms 45a, 45b are connected so as to be capable of rotating about one end thereof, with the other end of one of the arms (45a) fixed to the output shaft 44a of the rack receiving unit driving motor 44 and the other end of the other arm 45b rotatably connected to the rack receiving member 42.

When the motor 44 is driven and the retractable arm 45 retracts (i.e., the angle of intersection a (see FIG. 23) of both arms becomes smaller), the rack receiving member 42 moves to a rack receiving position (see FIG. 3 and FIG. 10) that is to the rear of the front surface of the gantry shaft 32.

Figure 16:
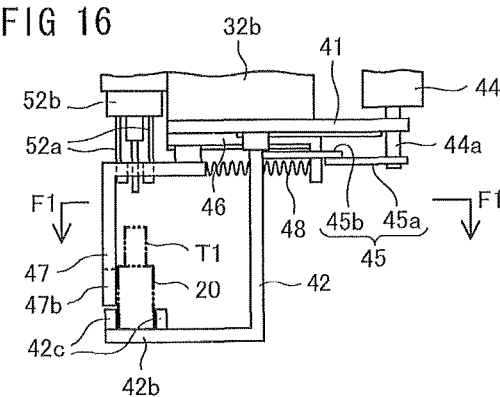
FIG. 16 is a side view diagram showing a main configuration of the sorting apparatus and is useful in explaining the operation of the sorting apparatus.

On the other hand, if the retractable arm 45 extends (i.e., the angle of intersection α of both arms becomes larger), the rack receiving member 42 moves to a blood collection tube removing position (or "vessel removing position", see FIG. 16) that is in front of the gantry shaft 32.

That is, in terms of the positional relationship with the gantry shaft 32, the rack receiving member 42 is capable of moving reciprocally between the rack receiving position and the blood collection tube removing position.

Once, in a state where the gantry shaft 32 of the transportation unit 30 has moved to the retreated position (refer to the position of the gantry shaft 32 shown by the solid line in FIG. 23), the rack receiving member 42 moves to the rack receiving position (see FIG. 3 and FIG. 14), the rack receiving member 42 is positioned at a rack delivery position (refer to the position P1 of the rack receiving member 42 in FIG. 23) where a rack 20 is delivered from the rack delivery device 60. Also, once, in a state where the gantry shaft 32 has been positioned at an advanced position (for example, the position of the gantry shaft 32 shown by the dot-dot-dash line in FIG. 23), the rack receiving member 42 moves to the blood collection tube removing position (see FIG. 16), the rack receiving member 42 is positioned at a sorting position (refer to the position P3 of the rack receiving member 42 in FIG. 23) where a blood collection tube T is loaded into a specified blood collection tube loading portion 70.

In terms of the positional relationship relative to the base portion 11 of the sorting apparatus 10, the rack receiving member 42 is capable of reciprocally moving between the rack delivery position and the sorting position. In this way, the sorting apparatus 10 is configured so that the rack 20 loaded on the rack receiving member 42 is transported in only the transportation direction X by the gantry shaft 32 and the rack receiving member 42. In other words, the rack receiving member 42 mounted on the gantry shaft 32 is a device to which the rack 20 is delivered and is not a device that receives a rack 20 through an operation made by itself. That is, a device for actively moving to receive the rack 20 is not mounted on the gantry shaft 32. Transferring of a rack 20 onto the rack receiving member 42 is carried out by an operation (raising/lowering operation) of the rack delivery device 60, described later. By using this configuration, it is possible to reduce the weight of a traveling section that includes the gantry shaft 32, there is no need to make the gantry shaft 32 especially rigid, and it is possible to make the gantry shaft 32, and in turn the transportation unit 30, lighter and more compact. The sorting apparatus 10 in which the configuration of the transportation unit 30 is compact in this way has a suitable construction for increasing the speed of the sorting process for blood collection tubes T loaded on the rack 20.

The rack receiving member 42 is a member that receives the rack 20 from the rack delivery device 60 and includes a first frame portion 42a that is supported so as to be suspended from the first guide rails 41,41 and a rack loading portion 42b that is supported at both ends by the first frame portion 42a. The first frame portion 42a has an inverted U shape when viewed from the front or from the rear (when viewed in the direction of the arrow FV in FIG. 3), and the rack loading portion 42b is disposed in a state so as to protrude to the front in the transportation direction from the lower end of the U-shaped first frame portion 42a. When viewed from the side (see FIG. 9), the rack receiving member 42 appears to be L shaped. The U-shaped first frame portion 42a also has a suitable size so as to allow a rack 20 on which the blood collection tubes T have been loaded to pass through in the front-rear direction.

Accordingly, in the rack receiving unit 40, a rack 20 on which the blood collection tubes T have been loaded can pass below the first frame portion 42a from the rear of the rack receiving member 42 and be loaded onto the rack loading portion 42b.

Also, protrusions 42c,42c for preventing positional displacements (i.e., for positioning) the loaded rack 20 in the front-rear direction (the same direction as the transportation direction) are installed on a rack loading surface that is the upper surface of the rack loading portion 42b.

The hold member 47 includes a second frame portions 47a supported so as to be suspended below the second guide rails 46,46 and a contact plate 47b that is attached to lower ends of the second frame portions 47a. The contact plate 47b is inverse U-shaped when viewed from the front or the rear (when viewed in the direction of the arrow FV in FIG. 3) and is disposed so as to be suspended downward from front sides of the second frame portions 47a. The hold member 47 appears to have an inverted L shape (like the Greek letter gamma) when viewed from the side (see FIG. 9), and is disposed so as to face the rack receiving member 42.

The contact plate 47b is disposed in front of the rack receiving member 42 positioned at the rack receiving position at a height where the contact plate 47b is capable of contacting a front side surface of a rack 20 loaded on the rack receiving member 42.

Tension springs 48 that pull the hold member 47 to the rear are connected to rear ends of the second frame portions 47a. Accordingly, in a state where no force is being applied from the outside (i.e., an "unloaded state"), the contact plate 47b of the hold member 47 is positioned at a rearmost position (or "separated position", see FIG. 3 and FIG. 9) of the movement range in the front-rear direction X. That is, the tension springs 48 energize the contact plate 47b of the hold member 47 toward the rearmost position.

The expression "rearmost position" of the contact plate 47b is a position that is to the front of the position of the rack 20 loaded on the rack receiving member 42 at the rack receiving position and to the rear of the position of the rack 20 loaded on the rack receiving member 42 at the blood collection tube removing position. Accordingly, the contact plate 47b of the hold member 47 positioned at the rearmost position is separated from the rack 20 loaded on the rack receiving member 42 at the rack receiving position.

Figure 15:
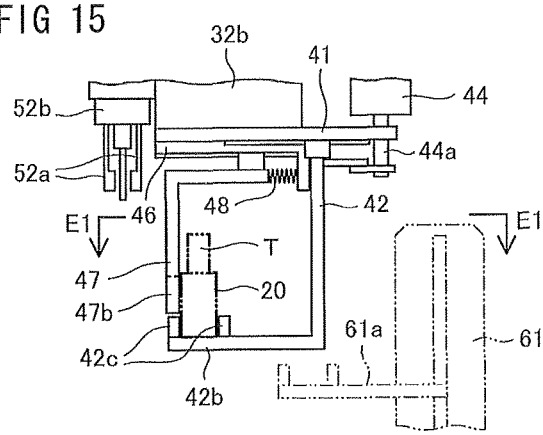
FIG. 15 is a side view diagram showing a main configuration of the sorting apparatus and is useful in explaining the operation of the sorting apparatus.

When the rack receiving member 42 that has received the rack 20 is moved from the rack receiving position to the blood collection tube removing position, at a point during such movement, the front side surface of the rack 20 loaded on the rack receiving member 42 contacts the contact plate 47b of the hold member 47 (see FIG. 15). Such contact is thereafter maintained even after the rack receiving member 42 has moved to the blood collection tube removing position (see FIG. 16). In this way, the hold member 47 whose contact plate 47b has contacted the rack 20 loaded on the rack receiving member 42 is positioned at the contact position.

Also, since the hold member 47 is pulled to the rear by the springs 48 as described above, the rack 20 contacted by the contact plate 47b of the hold member 47 will be sandwiched between the rack receiving member 42 and the hold member 47 while being subjected to a pressing force. That is, the rack 20 loaded on the rack receiving member 42 positioned at the blood collection tube removing position is securely held in a clamped state through the rack receiving member 42 and the hold member 47 operating in concert.

The transfer machine 50 transfers the blood collection tubes T of the rack 20 loaded on the rack receiving member 42 to blood collection tube loading portions 70 of a plurality of sorting cassettes 71 set on the sorting bench 72. The transfer machine 50 includes a slide mechanism 51 (see FIG. 3) installed on a front surface of the gantry shaft 32 so as to be capable of moving in the perpendicular direction Y that is perpendicular to the transportation direction X, an arm main body 52 that is installed on the slide mechanism 51, a blood collection tube gripping arm (or "vessel gripping arm") 52b that is installed on the arm main body 52, and a slide motor 53 for moving the slide mechanism 51.

Figure 17:
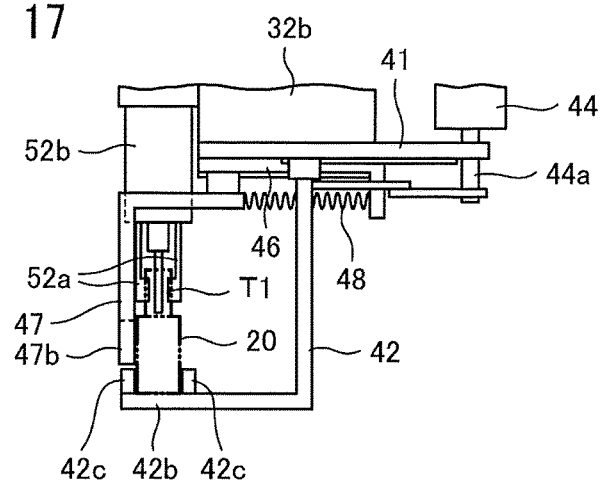
FIG. 17 is a side view diagram showing a main configuration of the sorting apparatus and is useful in explaining the operation of the sorting apparatus.

The blood collection tube gripping arm 52b is provided so as to be capable of moving toward and away from the arm main body 52 in the up-down direction and is capable of being moved by a raising/lowering motor (not shown) between an arm raised position (see FIG. 9) where the blood collection tube gripping arm 52b is at a highest position and a removal lowered position (see FIG. 17) and an insertion lowered position (see FIG. 20) where the blood collection tube gripping arm 52b has been lowered from the arm raised position.

The blood collection tube gripping arm 52b includes a pair of gripping arms 52a,52a that extend downward and are capable of opening and closing. Accordingly, by closing the pair of gripping arms 52a,52a, it is possible to grip the upper portion of a blood collection tube T, and by opening the pair of gripping arms 52a,52a, it is possible to transfer a blood collection tube T that was being gripped to a sorting destination, such as a blood collection tube loading portion 70.

The rack delivery device 60 is a device that delivers a rack 20 to the rack receiving member 42 of the sorting device 12 and includes a raising/lowering mechanism 61 (see FIG. 2 and FIG. 5) that raises and lowers a rack 20 before delivery and a conveyor unit 62 (see FIG. 2, FIG. 4, FIG. 5, and FIG. 24) that loads and unloads a rack 20 supplied from a rack storage unit, not shown, onto and off the raising/lowering mechanism 61.

Figure 4:
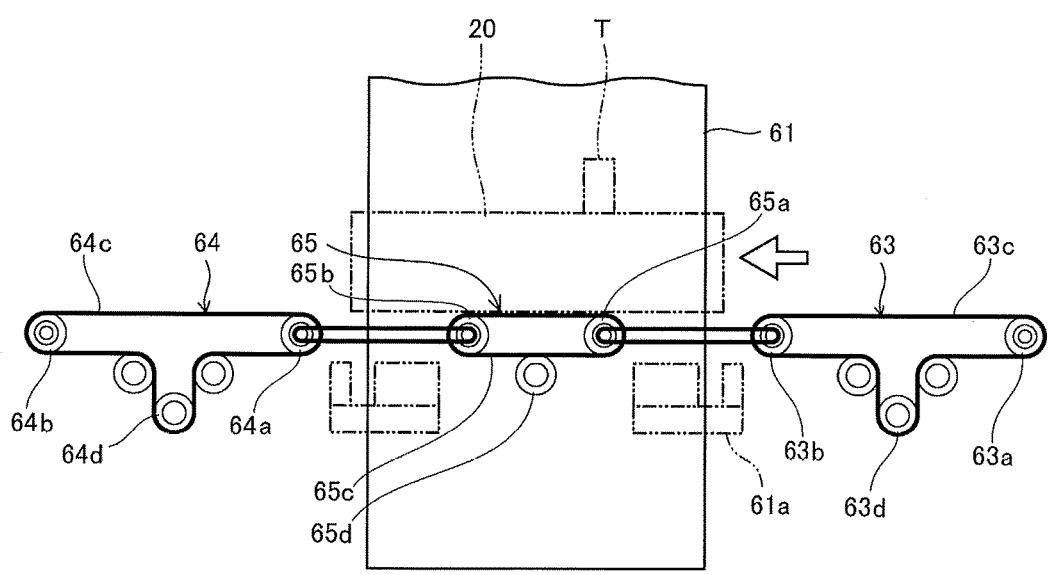
FIG. 4 is a partially enlarged, see-through arrow view taken in the direction A1 in FIG. 5.

As shown in FIG. 4, the conveyor unit 62 is disposed below the rack receiving unit 40 and is driven by a conveyor driving motor (not shown). The conveyor unit 62 includes a loading conveyor 63, an unloading conveyor 64 and a loading/unloading conveyor 65. The loading conveyor 63 conveys a rack 20 on which blood collection tubes T have been loaded onto the lifter 61a, described later, of the raising/lowering mechanism 61 and includes a driving roller 63a and a follower roller 63b, a loading belt 63c suspended between the two rollers 63a, 63b, and a tension roller unit 63d that applies tension to the loading belt 63c. The unloading conveyor 64 unloads a rack 20 after sorting and includes two follower rollers 64a, 64b, an unloading belt 64c, and a tension roller unit 64d. In the same way as the unloading conveyor 64, the loading/unloading conveyor 65 includes two follower rollers 65*a*, 65*b*, a loading/unloading belt 65*c*, and a tension roller unit 65*d*. The loading/unloading conveyor 65 is used during both loading and unloading and the rack 20 being loaded or unloaded is stopped and positioned on the loading/unloading conveyor 65.

The output shaft of the conveyor driving motor is connected to the driving roller 63*a* of the loading conveyor 63. The conveyor unit 62 includes timing belts 66, 67 for transmitting power between the conveyors 63, 64, and 65. The first timing belt 66 connects the follower roller 63*b* of the loading conveyor 63 and one of the follower rollers (65*a*) of the loading/unloading conveyor 65. That is, one of the follower rollers (65*a*) is a roller that drives the other of the follower rollers (65*b*) (in place of the driving roller 63*a* of the loading conveyor 63). The second timing belt 67 connects the other follower roller 65*b* of the loading/unloading conveyor 65 and one of the follower rollers (64*a*) of the unloading conveyor 64. That is, one of the follower rollers (64*a*) is a roller that drives the other of the follower rollers (64*b*) (in place of the driving roller 63*a* of the loading conveyor 63). Note that the timing belts 66, 67 are disposed at positions that do not interfere with the raising/lowering mechanism 61 that moves up and down. Accordingly, the raising/lowering operation of the raising/lowering mechanism 61 is not obstructed by the timing belts 66, 67.

The respective conveyors 63, 64, 65 are disposed so as to be aligned in a line from an upstream side to a downstream side in the rack transportation direction, with gaps being provided between adjacent conveyors. Such gaps are used as raising/lowering paths of the lifter 61*a* of the raising/lowering mechanism 61 that moves up and down. Accordingly, a forklift portion (or "scooping portion") 611*a* of the lowered lifter 61*a* is capable of moving below the transportation surface (upper surface) of the conveyor unit 62 via such raising/lowering paths. If, in a state where the forklift portion of the lifter 61*a* is positioned below the transportation surface of the conveyor, a rack 20 has been loaded onto and positioned on the loading/unloading conveyor 65, the lifter 61*a* will be positioned below the positioned rack 20. If the lifter 61*a* is raised in this state, the rack 20 will be transferred from the loading/unloading conveyor 65 to the lifter 61*a*. Also, if the lifter 61*a* holding an empty rack 20 after sorting is lowered to a position below the transportation surface of the conveyor unit 62, during such lowering the rack 20 will be transferred from the lifter 61*a* to the loading/unloading conveyor 65. After this, the empty rack after sorting is unloaded by the unloading conveyor 64 and once again a new rack is loaded onto and positioned on the loading/unloading conveyor 65. Note that the rack 20 after sorting does not need to be empty and blood collection tubes A that were not sorted may remain on the rack 20.

Accordingly, when the conveyor driving motor is operated, the loading conveyor 63 is driven and at the same time the rotation of the follower roller of the loading conveyor 63 is transmitted via the first timing belt 66 to one of the follower rollers of the loading/unloading conveyor 65, resulting in the loading/unloading conveyor 65 being driven. Also at the same time, the rotation of the other follower roller of the loading/unloading conveyor 65 is transmitted via the second timing belt 67 to one follower roller of the unloading conveyor 64, resulting in the unloading conveyor 64 being driven.

Note that the tension roller units of the loading conveyor 63 (and the unloading conveyor 64) include an inner roller that contacts an inner surface of the ring-shaped loading belt (or unloading belt) and two outer rollers that contact the outer surface of such belt, and the tension roller unit of the loading/unloading conveyor 65 is constructed from a single tension roller that contacts the outer surface of the ring-shaped loading/unloading belt. Since the tension roller units use a well-known configuration where the tension of the belts is adjusted by adjusting the pressing force exerted by the respective tension rollers on the belts (i.e., the contact pressure of such tension rollers), detailed description thereof is omitted here.

The raising/lowering mechanism 61 includes the lifter 61*a* that supports a rack 20 and is capable of raising and lowering the lifter 61*a* between a lifter lowered position (see FIG. 8 and FIG. 14) where the lifter 61*a* can receive a rack 20 from the loading conveyor 63 and a lifter raised position (see FIG. 9) where the rack 20 is delivered to the rack receiving member 42 at the rack delivery position.

The lifter lowered position and the lifter raised position of the lifter 61*a* are both set at height positions that do not interfere with the rack 20 loaded on the lifter 61*a* and the rack receiving member 42 that moves between the sorting position and the rack delivery position. The rack receiving member 42 is shaped so as to not interfere with the lifter 61*a* that has moved to a lifter raised position when the rack receiving member 42 moves toward the rack delivery position (see FIG. 3 and FIG. 6), so that it is possible to lower the lifter 61*a* from the lifter raised position to the lifter lowered position in a state where the rack receiving member 42 is positioned at the rack delivery position.

Accordingly, in the sorting apparatus 10 according to the present embodiment, it is possible, using the conveyor unit 62, to transport a rack 20 from a rack storage unit (not shown) to the lifter 61*a* positioned at the lifter lowered position and, by subsequently raising the lifter 61*a*, to deliver the rack 20 to the rack receiving member 42. With a construction where the lifter 61*a* is used to supply a rack 20 to the rack receiving member 42, it is easy to make the sorting apparatus 10 compact.

Note that since the transporting of the rack 20 between the rack storage unit and the conveyor unit 62 and the transporting of the rack 20 are well known, detailed description of such is omitted here.

Next, the operation of the sorting apparatus 10 according to the present embodiment will be described with reference to the explanatory diagrams in FIG. 5 to FIG. 22.

Figure 5:
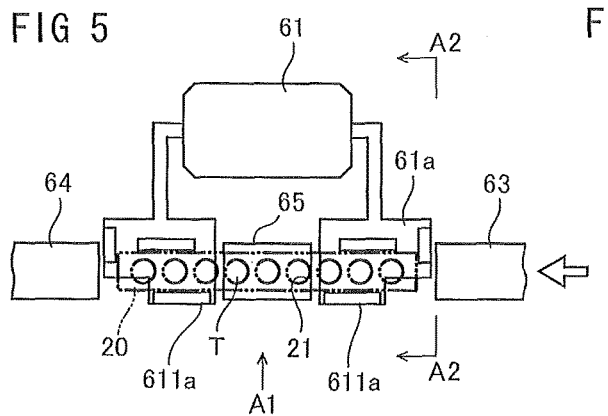
FIG. 5 is a plan view diagram showing a main configuration of the sorting apparatus and is useful in explaining the operation of the sorting apparatus.
Figure 8:
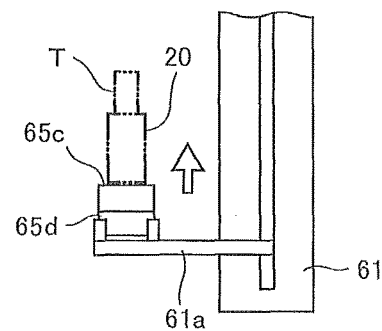
FIG. 8 is a side view diagram showing a main configuration of the sorting apparatus and is useful in explaining the operation of the sorting apparatus.
Figure 6:
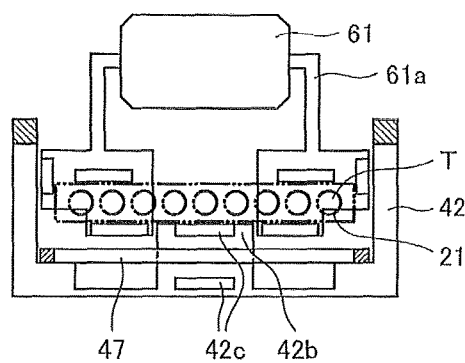
FIG. 6 is a plan view diagram showing a main configuration of the sorting apparatus and is useful in explaining the operation of the sorting apparatus.
Figure 9:
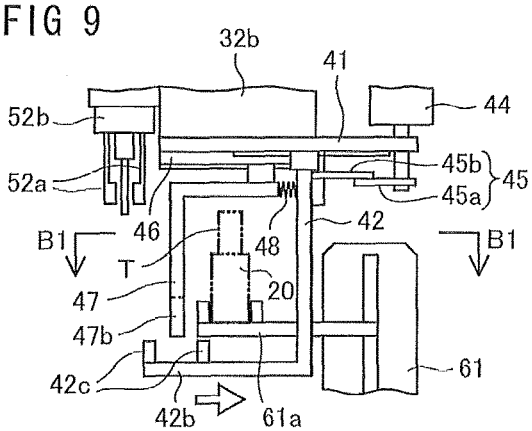
FIG. 9 is a side view diagram showing a main configuration of the sorting apparatus and is useful in explaining the operation of the sorting apparatus.
Figure 7:
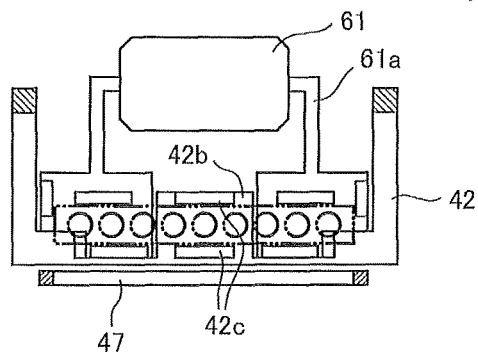
FIG. 7 is a plan view diagram showing a main configuration of the sorting apparatus and is useful in explaining the operation of the sorting apparatus.
Figure 10:
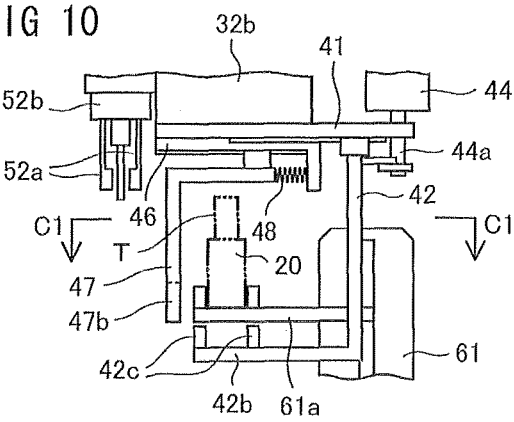
FIG. 10 is a side view diagram showing a main configuration of the sorting apparatus and is useful in explaining the operation of the sorting apparatus.
Figure 11:
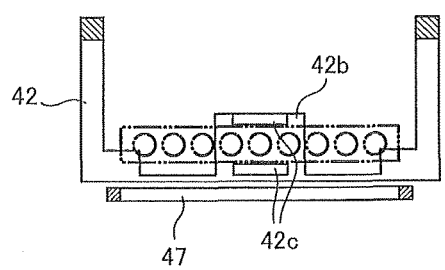
FIG. 11 is a plan view diagram showing a main configuration of the sorting apparatus and is useful in explaining the operation of the sorting apparatus.
Figure 12:
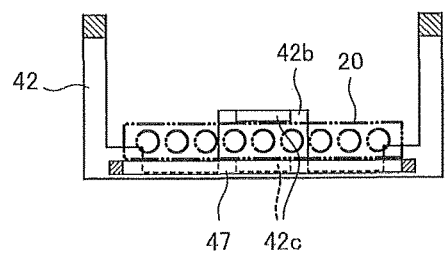
FIG. 12 is a plan view diagram showing a main configuration of the sorting apparatus and is useful in explaining the operation of the sorting apparatus.
Figure 13:
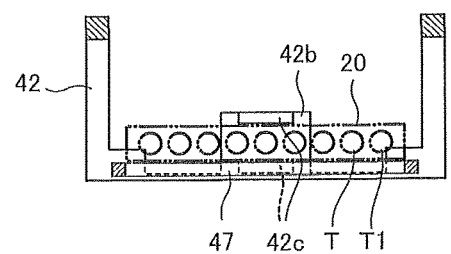
FIG. 13 is a plan view diagram showing a main configuration of the sorting apparatus and is useful in explaining the operation of the sorting apparatus.
Figure 14:
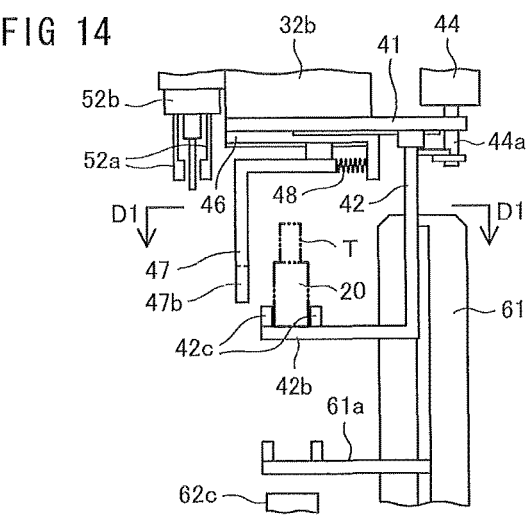
FIG. 14 is a side view diagram showing a main configuration of the sorting apparatus and is useful in explaining the operation of the sorting apparatus.

Note that FIG. 5 to FIG. 7 and FIG. 11 to FIG. 13 are plan views schematically showing states of the transportation unit 30, the rack receiving unit 40, and the transfer machine 50, and FIG. 8 to FIG. 10 and FIG. 14 to FIG. 22 are side views and cross-sectional views schematically showing states of the transportation unit 30, the rack receiving unit 40, and the transfer machine 50. FIG. 8 to FIG. 10 are side views corresponding to FIG. 5 to FIG. 7 and FIG. 14 to FIG. 16 are side views corresponding to FIG. 11 to FIG. 13. As examples, FIG. 6 is a cross-sectional view showing a cross section along the line B1-B1 in FIG. 9, FIG. 7 is a cross-sectional view showing a cross section along the line C1-C1 in FIG. 10, FIG. 8 is a side view showing a main configuration of the sorting apparatus viewed in the direction of the arrow A2 from the plane along the line A2-A2 in FIG. 5, FIG. 11 is a cross-sectional view showing a cross section along the line D1-D1 in FIG. 14, FIG. 12 is a cross-sectional view showing a cross section along the line E1-E1 in FIG. 15 and FIG. 13 is a cross-sectional view showing a cross section along the line B1-B1 in FIG. 16.

Here, the operation of the sorting apparatus 10 will be described with a rack supplying process, in which a rack 20 on which a plurality of blood collection tubes T have been loaded is loaded onto the lifter 61*a* by the loading conveyor 63 and the loading/unloading conveyor 65, as a starting point.

Note that when the rack supplying process is carried out, the lifter 61*a* is at the lifter lowered position (see FIG. 8), the gantry shaft 32 is at the retreated position (the position of the gantry shaft 32 shown by the solid line in FIG. 23), the rack receiving member 42 is at a rack loading/unloading withdrawn position (see FIG. 9), and the blood collection tube gripping arm 52*b* of the transfer machine 50 is at an arm raised position (see FIG. 9).

Note that the expression "rack loading/unloading withdrawn position" of the rack receiving member 42 is a position below the gantry shaft 32 where it is possible to raise and lower the lifter 61*a* on which a rack 20 has been loaded between the lifter lowered position and lifter raised position. Accordingly, as one example, the blood collection tube removing position of the rack receiving member 42 may be used as the rack loading/unloading withdrawn position. Also, since the rack loading portion 42*b* is disposed so as to protrude to the front in the transportation direction from the lower end of the first frame portion 42*a*, it is possible to move the front end of the rack loading portion 42*b* further to the front than the hold member 47 and at such time, there is no interference between the first frame portion 42*a* and the hold member 47.

In the rack supplying process, the rack 20 on which the plurality of blood collection tubes T have been loaded is loaded by the loading. conveyor 63 and the loading/unloading conveyor 65 onto the lifter 61*a* positioned at the lifter lowered position (see FIG. 5). At this time, the barcode information (or "sorting conditions") stuck onto the outer circumferences of the blood collection tubes T are read by the barcode reader 74 and the read information is transmitted to the controller 81. Based on the received barcode information, the controller 81 thereafter decides an advanced-to position in the transportation direction X of the gantry shaft 32 and/or a movement destination position in the perpendicular direction Y of the transfer machine 50.

After the rack supplying process has been completed, a rack delivery process is carried out.

In the rack delivery process, first, the lifter 61*a* on which the rack 20 has been loaded is raised to the lifter raised position (see FIG. 9).

Next, by driving the rack receiving unit driving motor 44 to retract the retractable arm 45, the rack receiving member 42 is moved back from the rack loading/unloading withdrawn position (see the arrow in FIG. 9) and is positioned at the rack receiving position (see FIG. 10). When doing so, since the gantry shaft 32 is at the retreated position, the rack receiving member 42 that moved to the rack removing position is positioned at the rack delivery position.

Next, the lifter 61*a* is lowered to the lifter lowered position (see FIG. 14).

By carrying out this operation, the rack 20 of the lifter 61*a* is loaded onto the rack loading portion 42*b* (see FIG. 3) of the rack receiving member 42 and delivery of the rack 20 is completed. Note that the front and rear of the lower end of the rack 20 loaded onto the rack loading portion 42*b* are held by being sandwiched by the protrusions 42*c*,42*c* of the rack loading portion 42*b*. By doing so, positional displacements of the rack 20 are prevented.

Once the rack delivery process has been completed, the first transporting process is carried out.

In the first transporting process, the gantry shaft 32 on which the rack receiving member 42 is installed is moved from the retreated position (see FIG. 23) in the transportation direction X to a specified advanced position (as one example, the position of the gantry shaft 32 shown by the dot-dot-dash line in FIG. 23). Once the gantry shaft 32 has moved to the advanced position, a specified blood collection tube loading portion 70 (for example, the blood collection tube loading portion 70*a* or 70*b*) becomes positioned directly below a movement path 52*r* of the transfer machine 50 (see FIG. 23).

In parallel with the first transporting process, a blood collection tube removal preparation process (or "vessel removal preparation process") is also carried out.

Note that at the start of the process, there are cases where one of the first transporting process and a blood collection tube removal preparation process has already started and cases where both processes start at the same time.

In the blood collection tube removal preparation process, by driving the motor 44 to extend the retractable arm 45, the rack receiving member 42 is moved in the transportation direction X from the rack receiving position to the blood collection tube removing position to the front.

While the rack receiving member 42 is moving during such process, the rack 20 loaded on the rack receiving member 42 contacts the contact plate 47*b* of the hold member 47 positioned in front of the rack receiving member 42 (see FIG. 12).

By doing so, the rack 20 on the rack receiving member 42 is held so as to be sandwiched between the protrusions 42*c* of the rack receiving member 42 and the hold member 47. In this way, in the sorting apparatus 10, by merely moving the rack receiving member 42 on which the rack 20 is loaded toward the blood collection tube removing position, the rack 20 loaded on the rack receiving member 42 is automatically held between the rack receiving member 42 and the hold member 47, which prevents the rack 20 from falling off.

The hold member 47 is capable of moving in the front-rear direction along the second guide rails 46,46 and is provided so as to be pulled toward the rear by the springs 48. Accordingly, after the rack 20 on the rack receiving member 42 has contacted the contact plate 47*b* of the hold member 47, it is possible to move the rack receiving member 42 even further to the front while maintaining the state where the rack 20 is held by the rack receiving member 42 and the hold member 47 (see FIG. 13 and FIG. 16). After this, the rack receiving member 42 becomes positioned at the blood collection tube removing position (see FIG. 16).

By doing so, the plurality of blood collection tubes T loaded on the rack 20 on the rack receiving member 42 also become positioned at the blood collection tube removing position. The blood collection tubes T positioned at the blood collection tube removing position also become positioned below the movement path 52*r* (see FIG. 2 and FIG. 23) of the blood collection tube gripping arm 52*b* of the transfer machine 50 that moves in the perpendicular direction Y.

The blood collection tube gripping arm 52*b* of the transfer machine 50 is moved above a blood collection tube T (refer, for example, to a blood collection tube T1 in FIGS. 13 and 16) to be removed out of the blood collection tubes T loaded on the rack 20 and the blood collection tube removal preparation process is completed.

In a state where the first transportation process and the blood collection tube preparation process have been completed, each blood collection tube T loaded on the rack 20 at the blood collection tube removing position becomes positioned at a sorting position (the position of the rack receiving member 42 shown at P3 in FIG. 23).

When the first transportation process and the blood collection tube removal preparation process have been completed, the blood collection tube removing process (or "vessel removing process") is carried out next.

Figure 18:
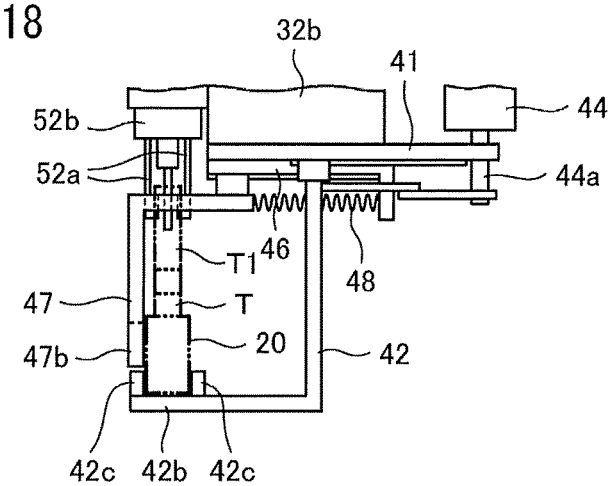
FIG. 18 is a side view diagram showing a main configuration of the sorting apparatus and is useful in explaining the operation of the sorting apparatus.

In the blood collection tube removing process, after being moved above the blood collection tube T1 to be removed, the blood collection tube gripping arm 52b of the transfer machine 50 is lowered to a removal lowered position, grips the blood collection tube T1 to be removed (see FIG. 17), and then the blood collection tube gripping arm 52b is raised to remove the blood collection tube T1 from the rack 20 (see FIG. 18).

When the blood collection tube removing process has been completed, next a blood collection tube transfer preparation process (vessel transfer preparation process) is carried out.

In the blood collection tube transfer preparation process, in a state where the removed blood collection tube T1 is gripped, the transfer machine 50 is moved in the perpendicular direction Y to position the gripped blood collection tube T1 above a specified blood collection tube loading portion 70 corresponding to the blood collection tube T1 (as examples, the blood collection tube loading portion 70a or 70b, see FIG. 23) (second transportation process).

Here, there are cases where the corresponding blood collection tube loading portion 70 is positioned below the rack receiving member 42 positioned at the sorting position (a case where the blood collection tube loading portion 70b is the specified transfer destination). In this case, the transfer machine 50 is moved in the perpendicular direction Y and the rack receiving member 42 positioned at the blood collection tube removing position is moved to the blood collection tube transfer withdrawn position (or "withdrawn position") (withdrawing process, see FIG. 19). When doing so, the hold member 47 that holds the rack 20 through cooperative operation with the protrusions 42c of the rack receiving member 42 is moved to the rear by the pulling force of the spring 48. Accordingly, it is possible to move the rack receiving member 42 to the blood collection tube transfer withdrawn position while maintaining the state where the rack 20 is held by the protrusions 42c of the rack receiving member 42 and the hold member 47. The hold member 47 is reliably moved toward the withdrawn position by the pulling force of the spring 48. Accordingly, the hold member 47 does not obstruct the raising/lowering operation of the blood collection tube gripping arm 52b.

Figure 19:
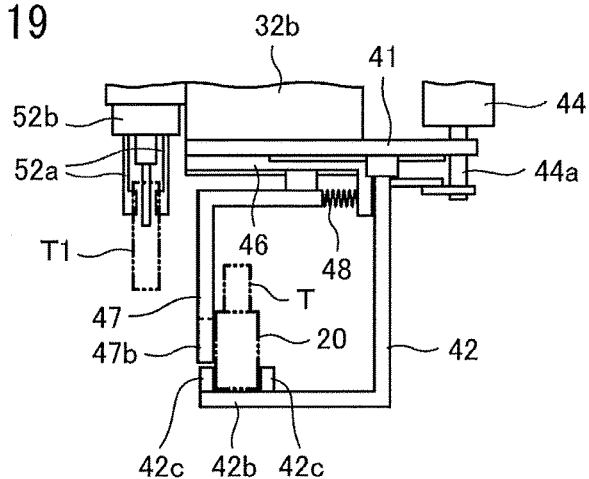
FIG. 19 is a side view diagram showing a main configuration of the sorting apparatus and is useful in explaining the operation of the sorting apparatus.

Note that the expression "blood collection tube transfer withdrawn position" of the rack receiving member 42 in the present embodiment refers to the position of the rack receiving member 42 shown in FIG. 19. In more detail, the expression "blood collection tube transfer withdrawn position" refers to a position where the rack receiving member 42 and the hold member 47 are positioned to the rear (above in FIG. 2) of the front surface (refer to the surface marked "FF" in FIG. 2) of the gantry shaft 32. In terms of the operation of the rack receiving member 42, this is a position where the rack receiving member 42 that has received the rack 20 at the rack receiving position (see FIG. 14) has moved forward and the front side surface of the rack 20 loaded on the rack receiving member 42 first contacts the contact plate 47b of the hold member 47 at the rearmost position of the hold member 47 (see FIG. 9).

In the sorting apparatus 10, since the rack receiving member 42 can move in the transportation direction X relative to the gantry shaft 32, it is possible to move the rack receiving member 42 to the blood collection tube transfer withdrawn position by merely moving the rack receiving member 42 in the transportation direction X. At this time, it is not necessary to move the gantry shaft 32 or to have the transfer machine 50 carry out any special operation.

When the rack receiving member 42 is moved to the blood collection tube transfer withdrawn position, the rack receiving member 42 and the hold member 47 become withdrawn from the movement path 52r of the blood collection tube gripping arm 52b of the transfer machine 50, which prevents interference between the rack receiving member 42 and the blood collection tube gripping arm 52b. That is, it is possible to lower the blood collection tube gripping arm 52b toward the blood collection tube loading portions 70 to the insertion lowered position (see FIG. 20).

In this way, in the sorting apparatus 10, since it is possible to move the rack receiving member 42 to the blood collection tube transfer withdrawn position, it is possible to load the blood collection tube T (T1) into an arbitrary blood collection tube loading portion 70 by merely moving the transfer machine 50 in the perpendicular direction Y.

If the movement direction of the transfer machine 50 can be limited to only the Y direction out of the X-Y directions, it is possible to use a configuration where the transfer machine 50 is moved along the beam portion 32b of the gantry shaft 32 that is the most fundamental component part of the sorting device 12, and possible to simplify the installation of the transfer machine 50. That is, it is possible to stably support the transfer machine 50 on the gantry shaft 32. With this construction, it is possible to suppress the vibration produced when the transfer machine 50 moves to a minimum and to increase the movement speed of the transfer machine 50. This means that the sorting apparatus 10 according to the present embodiment is an apparatus with a construction suited to operating at a higher speed.

When the blood collection tube transfer preparation process has been completed, a blood collection tube transferring process (vessel transferring process) is carried out next.

In the blood collection tube transferring process, the blood collection tube gripping arm 52b is lowered to the insertion lowered position and inserts the blood collection tube T1 gripped by the blood collection tube gripping arm 52b into the corresponding blood collection tube loading portion 70 (see FIG. 20).

Next, after the arm carries out an opening operation and the gripping of the blood collection tube T1 has been released, the blood collection tube gripping arm 52b is raised to the arm raised position and transferring of the blood collection tube T1 to a blood collection tube loading portion 70 is completed (see FIG. 19).

When the blood collection tube T (T1) is transferred in this way, the transportation unit 30 that moves in the transportation direction X is stopped and the main moving member is the transfer machine 50 that moves in the Y direction and the Z direction. If the moving parts are minimized in this way, the load applied to the moving parts when starting and stopping an operation is suppressed to a minimum. This construction is suited to increasing the transportation speed.

When the blood collection tube transferring process has been completed, a blood collection tube number confirming process (or "vessel number confirming process") is carried out next.

In the blood collection tube number confirming process, the number of blood collection tubes T remaining in the rack 20 of the rack receiving member 42 is confirmed. Here, if the remaining number is one or higher, the processing returns to the blood collection tube removal preparation process and the transferring process for the blood collection tubes T is carried out.

On the other hand, if the remaining number is zero, the blood collection tube transferring ending process (or "vessel transferring ending process") described next is carried out.

In the blood collection tube transferring ending process, the gantry shaft 32 retreats to the retreated position and the rack receiving member 42 is moved to the rack receiving position. By doing so, the rack receiving unit driving unit 43 moves to the rack delivery position.

After this, the lifter 61a is moved to the lifter raised position. By doing so, the empty rack 20 on the rack receiving member 42 is loaded onto the lifter 61a (see FIG. 21).

Next, the rack receiving member 42 is advanced (refer to the arrow in FIG. 21) and moved to the rack loading/unloading withdrawn position (see FIG. 22), and the lifter 61a is moved to the lifter lowered position (refer to the lifter position in FIG. 8). The empty rack 20 on the lifter 61a is transported by the unloading conveyor 64 and the loading/unloading conveyor 65. By doing so, the blood collection tube transferring ending process is completed, and a rack 20 on which a plurality of blood collection tubes T is loaded can be loaded. When the blood collection tube transferring ending process is completed, an operation ending confirming process is carried out.

If it is confirmed in the operation ending confirming process that the operation has ended, the sorting apparatus 10 stops. On the other hand, if the sorting operation is to continue, the processing returns to another rack supplying process.

In the sorting apparatus 10 according to the present embodiment, by executing operations according to the procedure described above, it is possible to carry out the sorting of vessels such as blood collection tubes T both accurately and at high speed.

However, as described earlier, the sorting apparatus 10 is configured so that the rack receiving member 42 and the transfer machine 50 are installed on the gantry shaft 32 in a state where such devices are capable of moving independently, the directions of movement of the rack receiving member 42 and the gantry shaft 32 match the X direction, and the direction of movement of the transfer machine 50 is the perpendicular direction Y that is perpendicular to the transportation direction X.

If the directions of movement of the rack receiving member 42 and the gantry shaft 32 are set as the same as the transportation direction X, the configuration will be resistant to the generation of complex vibration even if the gantry shaft 32 and the rack receiving member 42 are moved at the same time to transport a rack 20, so that the vibration produced during apparatus operation is suppressed to a minimum (refer to the blood collection tube removal preparation process).

Since the movement direction Y of the transfer machine 50 is set at a direction (the perpendicular direction Y) that is perpendicular to the direction of movement (the transportation direction X) of the rack receiving member 42, it is possible to move the rack receiving member 42 to the blood collection tube transferring withdrawn position and possible to use the transfer machine 50 that moves in only the perpendicular direction Y.

In addition, with the configuration described above, it is possible to make the transfer machine 50 a device that transports only the blood collection tubes T, making it unnecessary to transport the rack 20 with the transfer machine 50. That is, it is possible to reduce the weight to be transported by the transfer machine 50 to a minimum. If the transported weight is light, it is possible to reduce the weight and simplify the construction of the transfer machine 50 and the blood collection tube gripping arm 52b, so that the weight of the moving parts that move on the gantry shaft 32 can be suppressed to a minimum. By doing so, it is possible to make the configuration of the gantry shaft 32 more compact.

Note that the sorting apparatus 10 and the sorting method according to the present invention are not limited to the embodiment described above and the present invention further includes a variety of improved sorting apparatuses and the sorting methods within the scope of the present invention.

As one example, although the rack 20 used in the embodiment described above has six blood collection tube insertion portions 21 formed so as to be aligned in a row, it is possible to use a rack where the blood collection tube insertion portions 21 are formed in a plurality of rows, such as two rows or three rows.

Also, although the rack 20 used in the embodiment (see FIG. 26) includes blood collection tube insertion portions 21 that each have an access opening 21a at the top and a bottom holding portion 21b for holding the bottom of a blood collection tube T inserted from the access opening 21a, the rack that can be used by the sorting apparatus according to the present invention is not limited to a rack of such form.

It is possible to use any rack with a plurality of blood collection tube insertion portions that allow blood collection tubes to be loaded onto the rack by inserting the blood collection tubes from above the rack and allow the blood collection tubes to be removed from above the rack.

Figure 27:
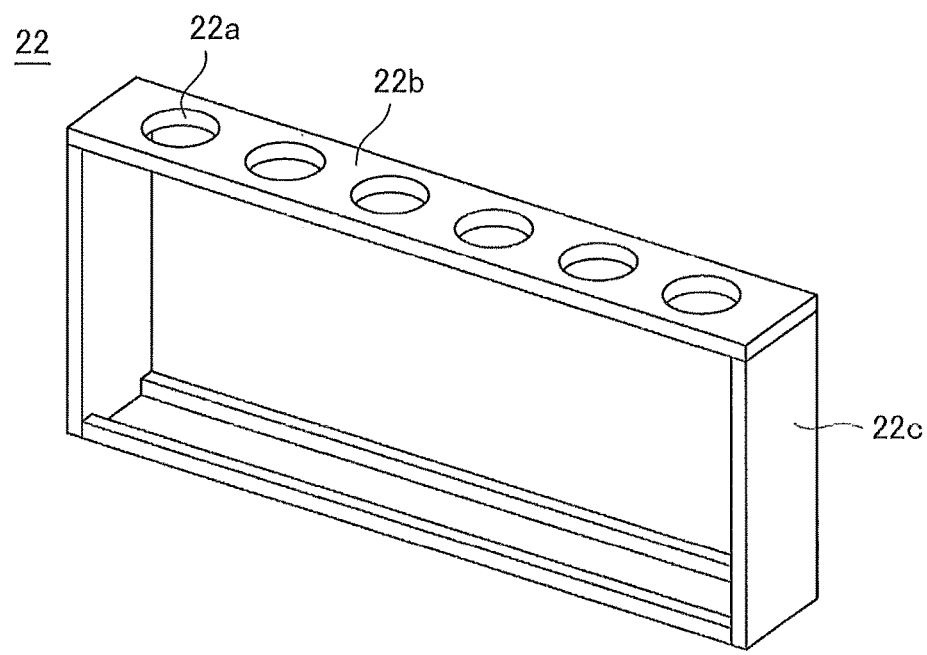
FIG. 27 is a perspective view showing a different rack to be used in the sorting apparatus.

For example, in a case where blood collection tubes equipped with brims on their outer circumferences are exclusively used, as shown in FIG. 27, it is possible to use a rack 22 with a blood collection tube support portion 22b (or "blood collection tube insertion portion") that has access openings 22a at the top and only a base portion 22c that supports the blood collection tube support portion 22b. With this rack 22 also, it is possible to insert the blood collection tubes from above the rack 22 and to load the blood collection tubes onto the rack 22 in a state where the brim portions (covers or the like) of the blood collection tubes are supported by the blood collection tube support portion 22b of the rack 22 and the blood collection tubes can be removed from above the rack.

Although not described in detail here, this also applies to the sorting cassette 71. That is, it is possible to use any sorting cassette 71 with a plurality of blood collection tube loading portions 70 that enable the blood collection tubes to be loaded onto the sorting cassette 71 by inserting the blood collection tubes into the blood collection tube loading portions 70 from above the sorting cassette 71 and enable the blood collection tubes to be removed from above the sorting cassette 71.

Also, although there are two positions, the rack loading/unloading withdrawn position and the blood collection tube transfer withdrawn position (or "withdrawn position") as positions to which the rack receiving member 42 withdraws in the embodiment described above, a single position may be used as a common withdrawn position.

It is also possible to sandwich and hold the rack 20 with the rack receiving member 42 and the hold member 47 more reliably by increasing the length of the protrusion 42c provided to the rear out of the protrusions 42c of the rack receiving member 42 in the embodiment described above and/or by providing an extension member that extend downward on part of a lower end of the contact plate 47b of the hold member 47. Note that such an extension member provided on the hold member 47 has a length set so as to not hit the rack loading portion 42b of the rack receiving member 42 and is disposed at a position that does not hit the protrusions 42c.

Also, although the timing at which the barcode information stuck onto the outer circumferences of the blood collection tubes T is read is the rack supplying process in the embodiment described above, the timing is not limited to such. As one example, barcode information may be read from the blood collection tubes T loaded onto a rack 20 on the loading conveyor 63 and transmitted to the controller 81 before the rack 20 is loaded onto the lifter 61a.

Various conditions could conceivably be used as determination conditions for the blood collection tube number confirming process. Although the number of blood collection tubes T remaining in the rack 20 on the rack receiving member 42 is confirmed in the embodiment described above, it is possible for example to confirm whether the number of blood collection tubes T that remain in the rack 20 on the rack receiving member 42 and require sorting is zero. In addition, if the blood collection tube transferring process is an operation decided in advance, the blood collection tube number confirming process may be omitted and the blood collection tube transferring ending process may be carried out as soon as the blood collection tube transferring process has ended.

The expression "vessel" used in this specification is not limited to containers, such as test tubes, that are provided with an opening and includes any container capable of holding a substance in any form.

The configuration of the conveyor unit is also not limited to the configuration in the embodiment described above.

As one example, the output shaft of the conveyor driving motor may be connected to a driving roller of the unloading conveyor 64, not the driving roller of the loading conveyor 63. The "connecting" referred to here is not limited to connecting with a timing belt and as examples may be a direct connection to a shaft or engagement of belts, gears, or the like.

The number of conveyor driving motors is not limited to one and may be plural. When two motors are used, for example, the output shafts of the respective motors may be connected to the driving roller of the loading conveyor 63 and the driving roller of the unloading conveyor 64. That is, if two conveyor driving motors are provided, as one example the other follower roller of the unloading conveyor 64 may be set as a driving roller. In such case, when the conveyor driving motor on the loading conveyor 63 side is driven, the loading conveyor 63 operates and at the same time, the rotation of the follower roller of the loading conveyor 63 is transmitted via the first timing belt to one follower roller of the loading/unloading conveyor 65 to drive the loading/unloading conveyor 65. At such time, the unloading conveyor 64 does not operate. Also, when the conveyor driving motor on the unloading conveyor 64 side is driven, the unloading conveyor 64 operates and at the same time, the rotation of the follower roller of the unloading conveyor 64 is transmitted via the second timing belt to the other follower roller of the loading/unloading conveyor 65 to drive the loading/unloading conveyor 65. At such time, the loading conveyor 63 does not operate.

In addition, although a three-conveyor configuration is used and independent transporting belts are used for each conveyor in the conveyor unit in the embodiment described above, it is also possible for the conveyor unit to be configured using a single transporting belt, for example. In such case, the transporting belt path is set so that gaps into which the lifter can be inserted can be produced between the position of the loading conveyor and the position of the loading/unloading conveyor and between the position of the loading/unloading conveyor and the position of the unloading conveyor.

What is claimed is:

1. A sorting apparatus comprising:
   a sorting device that receives and transports a rack on which a plurality of vessels are loaded, and that transfers the vessels loaded on the rack to predetermined vessel loading portions; and
   a delivery device that delivers the rack to the sorting device,
   wherein the sorting device includes:
   a transportation unit including a gantry shaft that extends in a first horizontal direction in a horizontal plane and that is movable in a second horizontal direction, wherein the second horizontal direction is in the horizontal plane and is perpendicular to the first horizontal direction,
   a rack receiving unit including a rack receiving member that is installed on a lower surface of the gantry shaft and on which the rack is loaded,
   a transfer unit that is installed on a side surface of the gantry shaft, is movable along in the first horizontal direction, and is raisable to remove the vessels from the rack loaded on the rack receiving member and transfer the vessels to the predetermined vessel loading portions; and
   the rack receiving unit further includes a driving member that includes a first motor and a retractable arm member that is connected to the first motor, and the retractable arm member moves the rack receiving unit by retracting in the second horizontal direction.

2. The sorting apparatus according to claim 1, wherein the transfer unit includes:
   a slide mechanism installed on a front surface of the gantry shaft,
   a second motor that moves the slide mechanism, and
   an arm main body that is raisable and lowerable and is configured to grip the vessels.

3. The sorting apparatus according to claim 2,
   wherein the rack receiving member is movable to a rack receiving position to receive the rack from the delivery device, to a vessel removal position where the vessels in the rack are removed by the transfer unit, and to a withdrawn position that is between the rack receiving position and the vessel removal position and where interference between movement of the arm main body and the rack receiving unit is prevented.

4. The sorting apparatus according to claim 1,
   wherein a movement range of the gantry shaft in the second horizontal direction is shorter than a reciprocal movement range of the rack receiving unit.

5. The sorting apparatus according to claim 1,
   wherein the delivery device includes a conveyor unit that transports the rack in the first horizontal direction and a lifter that removes the rack from the conveyor unit and raises/lowers the rack.

6. A vessel sorting method for a sorting apparatus that receives and transports a rack on which a plurality of vessels are loaded, and that transfers the vessels loaded on the rack to predetermined vessel loading portions; the sorting apparatus including a transportation unit including a gantry shaft that extends in a first horizontal direction in a horizontal plane and that is movable in a second horizontal direction, wherein the second horizontal direction is in the horizontal plane and is perpendicular to the first horizontal direction, a rack receiving unit including a rack receiving member that is installed on a lower surface of the gantry shaft and on which the rack is loaded, a delivery device that delivers the rack to the sorting device, and a transfer unit that is installed on a side surface of the gantry shaft, is movable along in the first horizontal direction, and is raisable to remove vessels from the rack loaded on the rack receiving member and transfer the vessels to a predetermined vessel loading portion, the rack receiving unit further includes a driving member that includes a first motor and a retractable arm member that is connected to the first motor, and the retractable arm member moves the rack receiving unit by retracting in the second horizontal direction, the vessel sorting method comprising:

holding the rack on the rack receiving member by a hold member that is installed on a lower surface of the gantry shaft and includes a contact part that comes into contact with a side surface of the rack loaded on the rack receiving member, the hold member including an energizing device energizing the contact part toward the side surface of the rack, wherein the contact part acts in concert with the rack receiving member on the rack to hold the rack on the rack receiving member;

a first transportation process where, after the rack on which a plurality of vessels are loaded has been received by the rack receiving unit, the transportation unit on which the rack receiving unit is installed transports the rack by linearly moving in the second horizontal direction from a rack receiving position to a transfer position where a vessel loaded on the rack is removed;

a vessel removal preparation process of moving the rack receiving unit via the first motor and the retractable arm member in the second horizontal direction and positioning the rack receiving unit at a lowered position on a movement path of the transfer unit which is installed so as to be movable in the first horizontal direction so as to position a vessel loaded on the rack loaded at the lowered position;

a vessel removing process removing a predetermined vessel out of the vessels moved to the lowered position by raising and lowering a vessel gripping arm provided in the transfer machine;

a vessel transfer preparation process positioning a predetermined vessel gripped by the vessel gripping arm above a vessel loading unit by moving the transfer unit that has removed the predetermined vessel in the first horizontal direction; and a vessel transfer process lowering the vessel gripping arm to load the predetermined vessel gripped by the vessel gripping arm into the vessel loading portion.

7. The vessel sorting method according to claim 6, wherein the vessel transfer preparation process includes:

a second transportation process that moves the transfer unit above the vessel loading portion positioned below the rack receiving unit positioned at the lowered position on the movement path of the transfer unit; and a withdrawing process that moves the rack receiving unit at the lowered position on the movement path of the transfer unit toward the rack receiving position to withdraw the rack receiving unit from the lowered position.

* * * * *